United States Patent [19]

Young et al.

[11] Patent Number: 4,966,874

[45] Date of Patent: Oct. 30, 1990

[54] PROCESS FOR PREPARING LINEAR ALPHA-OLEFINS USING ZIRCONIUM ADDUCTS AS CATALYSTS

[75] Inventors: David A. Young; Larry O. Jones; Troy J. Campione, all of Baton Rouge, La.

[73] Assignee: Exxon Chemical Patents Inc., Linden, N.J.

[21] Appl. No.: 325,878

[22] Filed: Mar. 20, 1989

Related U.S. Application Data

[60] Division of Ser. No. 195,665, May 18, 1988, Pat. No. 4,855,525, which is a continuation-in-part of Ser. No. 63,662, Jun. 19, 1987, abandoned.

[51] Int. Cl.$^5$ ............................................. B01J 31/38
[52] U.S. Cl. ................................... 502/117; 585/522; 585/523
[58] Field of Search ......................................... 502/117

[56] References Cited

U.S. PATENT DOCUMENTS

| | | | |
|---|---|---|---|
| 3,178,401 | 4/1965 | Coover et al. | 502/117 X |
| 3,213,073 | 10/1965 | Coover et al. | 502/117 X |
| 3,230,208 | 1/1966 | Coover et al. | 502/117 X |
| 3,316,229 | 4/1967 | Vandenberg | 502/117 X |
| 3,468,856 | 9/1969 | Asai et al. | 502/117 X |
| 3,496,158 | 2/1970 | Fisher et al. | 502/117 X |
| 3,622,552 | 11/1971 | Fukuda et.al. | 502/117 X |
| 3,670,043 | 6/1972 | Kubicek et al. | 502/117 X |
| 4,066,571 | 1/1978 | Columberg | 502/117 X |

FOREIGN PATENT DOCUMENTS 62-430  1/1987  Japan .

*Primary Examiner*—Patrick P. Garvin
*Attorney, Agent, or Firm*—J. J. Mahon

[57] ABSTRACT

Linear alpha-olefins are prepared by the oligomerization of ethylene using a two component catalyst system comprising (a) a soluble adduct of zirconium tetrahalide, the halogen being Br or Cl, with an organic compound selected from the group of esters, ketones, ethers, amines, nitriles, anhydrides, acid chlorides, amides or aldehydes, the organic compound having up to about 30 carbon atoms and (b) an alkyl metal selected from the group $R_2AlX$. $RAlX_2$, $R_3Al_2X_3$, $R_3Al$ and $R_2Zn$ where R is $C_1$–$C_{20}$ alkyl and X is Cl or Br. $ZrCl_4$ adducts with organic acetates are the preferred embodiments.

4 Claims, No Drawings

PROCESS FOR PREPARING LINEAR ALPHA-OLEFINS USING ZIRCONIUM ADDUCTS AS CATALYSTS

This application is a division of Ser. No. 195,665, filed May 18, 1988, now U.S. Pat. No. 4,855,525, issued Aug. 8, 1989 which is a continuation-in-part of Ser. No. 063,662, filed Jun. 19, 1987, now abandoned.

This invention relates to an improved process for preparing linear alpha-olefins from ethylene. More particularly, this invention relates to the production of such linear alpha-olefins utilizing an adduct of zirconium tetrahalides as an essential part of the homogeneous catalyst system.

The oligomerization of ethylene to produce linear alpha-olefins is generally known in the art. The use of zirconium-containing catalysts is disclosed, for example, in U.S. Pat. Nos. 4,486,615; 4,442,309; 4,434,313; 4,434,312; 4,410,750; 4,409,409; 4,396,788; 4,377,720 and 4,361,714. A number of these patents disclose reaction products of zirconium halides to provide zirconium alkoxides or carboxylates, such as U.S. Pat. Nos. 4,409,409 and 4,486,615 which show various derivatives of tetravalent zirconium. The concept of the present invention, use of zirconium tetrahalide (bromide, chloride or mixtures thereof) adducts of certain organic compounds, preferably certain alkyl acetate esters, as a catalyst for linear alpha-olefin preparation, is not disclosed by these references.

Japanese Application 60-137683, filed Jun. 25, 1985 by Shiroki et al. and published Jan. 6, 1987 as Japanese Kokai 62-000430, discloses the production of linear alpha-olefins by polymerizing ethylene in the presence of a mixture consisting of a zirconium halide, an alkyl aluminum halide and a compound which may be that of sulfur or that of nitrogen. The catalyst is described as a three component catalyst.

U.S. Pat. No. 3,622,552, issued Nov. 23, 1971 to Fukuda et al. discloses the preparation of crystalline homo- or co-polymers of olefin using a three component catalyst comprising (1) an organoaluminum compound of the formula $AlR_2X$, R being a hydrocarbyl, X being halogen, (2) a Group IV, V or VI transition metal halide and (3) a saturated or unsaturated carboxylic ester having a side chain on a carbon atom in alpha position to ester carbon atoms. Fukuda et al. do not disclose the preparation of linear alpha-olefin oligomers and do not disclose the formation of a homogeneous two component catalyst, one component of which being an adduct of zirconium tetrahalide with an organic compound.

It is known in the art to use insoluble Ziegler-type catalysts in heterogeneous catalysis to produce high molecular weight, high density polymers. A characteristic of such reactions is that in the formation of the resultant insoluble catalytic complex the metal is reduced to a lower valence. An example is the reaction between titanium tetrachloride, aluminum chloride and triethyl aluminum wherein the titanium metal is reduced to the +3 valence state.

It is also know in the art to modify a heterogeneous Ziegler-type catalyst to improve stereospecificity toward a desired crystalline structure, such as controlling selectivity to isotactic polypropylene. Fukuda et al., noted above, use a third component such as methyl methacrylate for this purpose and report increases in the percentage of heptane insolubles which is evidence of high molecular weight polymer. Boor, in "Ziegler-Natta Catalysts and Polymerizations", (N.Y.:Academic Press, 1978) at page 228 reports the effects of a number of third components, including the Fukuda et al. third component, on the isotacticity of polypropylene and polybutene-1 products.

The present invention is concerned with a homogeneous catalyst system for conducting the oligomerization of ethylene to prepare linear alpha-olefins. In the present invention the objective is toward alpha-olefin selectivity and not the production of high molecular weight, crystalline polymers. It is known in the art that the oligomerization of ethylene to form alpha-olefins proceeds by a mechanism which is different from that in which stereoregular high polymers are formed. Reference may be made to Langer in J. Macromol. Sci-Chem. A4(4), pages 775–787 (July, 1970), at page 776 where it is noted that a reduced, insoluble Ziegler catalyst produces high molecular weight polyethylene, but that a soluble catalyst is required in order to have ethylene oligomerization. Boor, cited above, notes at page 606 that an oligomerization "catalyst functions only if alkylation, but not precipitation, is allowed to take place".

$ZrCl_4$ adducts per se, including adducts with esters have been disclosed in the literature. B. Kletenik et al. in Zkur.Obschchel.Khim.29, 13–17 (1959) disclose the preparation of complex compounds generalized by the formula $ZrCl_4 RCOOR_1$ in benzene solutions from equimolar amounts of $ZrCl_4$ and esters. However, no use in ethylene oligomerization is disclosed. Other references disclosing addition compounds of $ZrCl_4$ with organic compounds are: Graven et al., J. lnorg, Nucl. Chem. 31(6), 1743–8 (1969), which shows additions with ethers, esters, ketones and others and Hummers et al., J. Am. Chem Soc 74, 5277–9 (1952) which shows complexes with various benzoate esters. Neither of these references show any use as catalysts in ethylene oligomerization.

A general review of commercially used ethylene oligomerization processes for linear alpha-olefins is found in Kirk-Othmer, Encyclopedia of Chemical Technology, Third Edition, Volume 16, pages 487–499 (1981:John Wiley & Sons, Inc.).

An objective of the present invention is to provide a novel catalyst system for the oligomerization of ethylene to produce linear alpha-olefins having a high degree of linearity, such as about 90 mole percent or greater within a desirable molecular weight range, i.e., oligomers of 4 to 50 carbon atoms. A high degree of linearity is important because the oligomers so produced are used as raw materials for preparing surfactants, such as ethoxylated linear alcohols, and linearity is critical in order for the surfactants to have suitable biodegradability.

The present invention provides a number of desirable advantages: the catalyst is readily prepared and is soluble, it may be used in high concentrations, it is storage stable and use of the novel adduct catalyst system provides linear products with suitable conversions of ethylene. The solubility of the novel catalyst of this invention enables the catalyst to be fed to the reaction vessel in an easily controlled liquid stream. Importantly the catalyst exhibits complete solution into the system and all the zirconium is available for catalysis in contrast to prior art techniques wherein zirconium was added as a partially soluble salt. The catalyst also exhibits high activity and productivity and requires relatively smaller amounts of co-catalyst than prior art catalysts in order to produce linear oligomers in a given molecular weight range.

In accordance with the present invention there has been discovered a process for preparing a reaction product comprising substantially linear alpha-olefins of Mn (number average molecular weight) 70 to about 700 by oligomerizing ethylene in the presence of a novel homogeneous two component catalyst, the first component being an adduct of $ZrCl_aBr_b$, where $a+b=4$ and a or b may be 0, 1, 2, 3 or 4, with an organic compound selected from the group consisting of esters, ketones, ethers, amines, nitriles, anhydrides, acid chlorides, amides or aldehydes, said organic compound having up to 30 carbon atoms, and the second component being an alkyl metal catalyst selected from the group consisting of $R_2AlX$, $RAlX_2$, $R_3Al_2X_3$, $R_3Al$ and $R_2Zn$ wherein R is $C_1$–$C_{20}$ alkyl and X is Cl or Br, the oligomerization being conducted in a reactor vessel at 50° C. to 300° C. at a pressure of about 500 to 5,000 psig in a solution of $C_2$–$C_{100}$ alpha-olefin or a liquid inert solvent which is not reactive with said catalyst and in which said two component catalyst is soluble.

The essential aspect of the present invention is the first component of the catalyst, an adduct of zirconium tetrahalide, the halogen being Br or Cl or a mixture of said halides, with certain organic compounds. The second component catalyst, which is an alkyl aluminum or alkyl zinc compound, is well known in the art and has been used conventionally in ethylene oligomerization processes as a co-catalyst component.

The first component of the catalyst may be an adduct of $ZrCl_aBr_b$ with an ester, a ketone, an ether, an amine, a nitrile, an anhydride, an acid chloride an amide or an aldehyde and these various adduct-forming organic components may have up to about 30 carbon atoms. The adducts generally include mole ratios of organic component to zirconium of from about 0.9 to 1 up to about 2 to 1. Preferred are equimolar adducts. The adduct must be soluble in and stable in the solvent which is used as the reaction medium for the oligomerization process of the present invention.

Adducts may be formed from $ZrCl_4$, $ZrBr_4$, as well as the mixed tetrahalides: $ZrClBr_3$, $ZrCl_2Br_2$ and $ZrCl_3Br$, wherein the halogen is limited to Cl or Br. $ZrCl_4$ adducts are especially preferred.

Preferred are adducts of $ZrCl_4$ with esters of the general formula $R_1COOR_2$ where $R_1$ and $R_2$ may be alkyl, aryl, alkaryl or aralkyl groups having a total of 1 to 30 carbon atoms and Rl may also be hydrogen. $R_1$ and $R_2$ taken together may also represent a cycloaliphatic group and the ester may be compounds such as gammabutyrolactone or phthalide. Especially preferred are alkyl acetate esters where the alkyl group has 6 to 16 carbon atoms such as n-hexyl acetate, n-heptyl acetate, n-octyl acetate, n-nonyl acetate, n-decyl acetate, isohexyl acetate, isodecyl acetate, and the like which have been found to form discrete dimeric equimolar adducts with $ZrCl_4$. This particularly preferred embodiment may be represented by the formula $(ZrCl_4.CH_3COOR_1)_2$ where $R_1$ is a $C_6$ to $C_{16}$ alkyl or a mixture of $C_6$ to $C_{16}$ alkyls These preferred ester adducts are capable of providing highly concentrated solutions in the solvent used as the reaction solvent, i.e., up to about 40% by weight of $ZrCl_4$, when preferred mixed isodecyl acetate esters are used. Particularly useful are mixtures of various isomers of isohexyl, isoheptyl, isooctyl, isononyl, isodecyl or isotridecyl acetate sold by Exxon Chemical Company, respectively, as Exxate® 600, Exxate® 700, Exxate® 800, Exxate® 900, Exxate® 1000 and Exxate® 1300. The isohexyl acetate mixture comprises about, by weight, 36–38% n-hexyl acetate, 18–20% 2-methyl-1-pentyl acetate, 22–24% 3-methyl-1-pentyl acetate and 16–18% 4-methyl-1-pentyl acetate as principal compounds. Exxate® 1000 isodecyl acetate mixture is a complex mixture of isomers and gas chromatoraphic analysis shows about 100 different isomers being present, none of which are greater than about 12% by weight of the mixture. Exxate® 1000 has a boiling point range of about 425° F. to 482° F. (95% distilled).

These adducts have been prepared by simple addition of the organic ester to a mixture of $ZrCl_4$ in the inert organic or alpha-olefin solvent. The ester is added slowly to the stirred mixture at room temperature and complete formation and dissolution of the adduct is observed after several minutes. The dissolution is exothermic and the mixture reaches a temperature of about 50° C. as a result of the heat of reaction due to adduct formation.

Also, suitable for providing soluble zirconium adducts useful as the first component catalyst of the present invention are ketones, ethers and aldehydes which may be represented, respectively, by the formulas: $R_1C(:O)R_2$, $R_1OR_2$ and $R_1C(:O)H$ where $R_1$ and $R_2$ represent alkyl, aryl, alkaryl or aralkyl groups, the total of $R_1$ and $R_2$ being not more than about 30 carbon atoms. Also suitable are primary, secondary and tertiary amines wherein the hydrocarbyl radicals have up to about 30 carbon atoms, such as n-dodecyl amine and tri-n-hexyl amine. Also suitable are hydrocarbyl cycloaliphatic ethers and ketones having from 4 to 16 carbon atoms, e.g., cyclohexanone.

Other adduct-forming organic compounds useful in the present invention include nitriles, anhydrides, acid chlorides and amides having up to 30 carbon atoms. These may be represented, respectively, by the formulas $RC\equiv N$, $(R(C:O))_2O$ $RC(:O)Cl$ and $RC(:O:NH_2$, $RC(:O)NHR$ or $RC(:O)NR_2$ where R represents a hydrocarbyl alkyl, aryl, alkaryl or an aralkyl group having up to about 30 carbon atoms. Examples are adducts of $ZrCl_4$ with n-undecane nitrile, n-decyl succinic anhydride and n-decanoyl chloride.

The second catalyst component of the present invention is an aluminum alkyl of the formulas $R_2AlX$, $RAlX_2$, $R_3Al_2X_3$, $R_3Al$ or a zinc alkyl of the formula $R_2Zn$, where $R_1$, $R_2$ and $R_3$ may be $C_1$–$C_{20}$ alkyl and X is Cl or Br. Diethylaluminum chloride, aluminum ethyl dichloride and mixtures thereof are preferred.

The two-component catalyst composition per se as a composition of matter is another embodiment of the present invention.

The process of the present invention is conducted under generally conventional oligomerization conditions of temperature and pressure, that is, about 50° C. to 250° C. and about 500–5000 psig, preferably 1000 to 3500 psig.

The process is conducted in solution in an inert solvent which must be non-reactive with the catalyst system or in the presence of a solvent comprising a liquid alpha-olefin, particularly $C_6$–$C_{100}$ alpha-olefins. Suitable solvents include aromatic or aliphatic hydrocarbons and halogenated aromatics such as chlorobenzene, dichlorobenzene and chlorotoluene. Preferred solvents are toluene, xylenes and $C_3$–$C_{24}$ alkanes, especially heptane. Mixtures of these solvents may also be used.

Liquid alpha-olefins, as noted above, may be used as solvents for the process and these may include liquid alpha-olefins which are formed in the process, especially $C_6$–$C_{30}$ alpha-olefins, which may be used as the reaction medium or as a solvent for the catalyst components and the feedstock and used to introduce these materials into the reactor vessel.

Such alpha-olefins may also be used as a solvent in the process of this invention in admixture with the aforesaid non-reactive aromatic or aliphatic solvents. A useful mixture comprises a minor proportion of $C_4$–$C_{30}$ alpha-olefins, such as about 10% by weight of $C_8$ and $C_{10}$ alpha-olefins and 0–5% by weight of $C_4$ alpha-olefins, based on the amount of ethylene feedstock, with the balance of the solvent being xylene. The use of this solvent mixture with solvent recycle improves distillation efficiencies during product recovery.

The use of liquid alpha-olefins as a recycled solvent in the process of this invention constitutes a further embodiment. An olefin product, after being recycled through the reaction system, becomes substantially branched. This occurs as a result of the buildup of the branched olefins and the continued reaction of the linear olefins to form substantially branched olefins of higher carbon numbers. These branched olefins are substantially inert to further reaction with ethylene or undergo further reaction with ethylene to only a very minor extent. Thus, the recycled branched alpha-olefins will achieve an essentially steady state condition with minimal effects upon ethylene consumption and desired linear alpha-olefin product quality, thereby enabling such recycled substantially branched alpha-olefins to be employed effectively as a solvent for the process of this invention.

To facilitate the separation of linear alpha-olefin product from substantially branched alpha-olefin recycle solvent, the branched alpha-olefin recycle solvent should have a molecular weight higher than that of the desired linear alpha-olefin product. Thus, the use as a solvent of a recycle stream comprised principally of substantially branched $C_{20}$ alpha-olefins is advantageous in the process of this invention when it is desired to produce $C_4$ to $C_{18}$ linear alpha-olefin products. The recycling of the branched $C_{20}$ alpha-olefins results in a recycle solvent which is readily separated from the linear alpha-olefin product being manufactured.

The feed and catalyst components may be introduced in any order into the reactor vessel, but preferably the ethylene (in solvent) and the solution of zirconium tetrahalide adduct are first combined prior to introducing the second component catalyst, which is also in solution.

As is known in the art, the temperature and pressure of the oligomerization reaction may be varied to adjust the molecular weight, linearity and yield of the desired product. As is also known, molecular weight (Mn) of desired product is controlled through adjustment of the molar ration of aluminum to zirconium.

The preferred temperature range to obtain high quality linear alpha-olefin polymer averaging between 6 to 20 carbon atoms is about 120° C. to 250° C. At these preferred temperatures, the pressure should be about 1000 psig in a continuous stirred tank reactor, which will produce about 20% conversion of ethylene with the production of high molecular weight polyethylene being limited to less than about 0.1 wt. % in the product. In a tubular reactor, conversions of 65–80% ethylene at about 120 C-250.C with pressures of about 3000 psig are feasible, based on reactor modeling studies. Under the foregoing preferred conditions, a linearity of greater than 95 mole % can be obtained.

The amount of catalyst used in the present invention relative to the ethylene feedstock may be expressed as the weight ratio of ethylene feedstock to zirconium. Generally, the range is about 10,000 to 120,000 grams of ethylene per gram of zirconium present in the catalyst composition, with the preferred range being about 25,000 to 35,000 grams of ethylene per gram of zirconium, most preferably about 31,000 grams of ethylene per gram of zirconium. These ranges are determined primarily by processing concerns such as catalyst removal from product, catalyst cost and the need to minimize the amount of water which will be present.

In practicing the process of the present invention, the presence of water in the system should be minimized, since the catalyst of this invention is particularly sensitive to the presence of water. It has been found that only minor amounts of water will tend to produce undesirable quantities of high molecular weight polyethylene and will reduce conversions to the desired linear alpha-olefin oligomer product. The amounts of water are best controlled with respect to the molar ratio of zirconium to water in the reaction mixture. The amount of water present is preferably in the range of about 2000 to 1 to about 10,000 to 1 moles of zirconium per mole of water or higher. Within these desired ranges the percentage of high molecular weight (greater than 10,000) polyethylene is between 0.017 and 0.04 wt. %, based on the weight of product with conversions to product being in the range of about 55 to 70%. However, at $Zr/H_{20}$ mole ratios of 20 to 50 to or less, while a conversion to desired oligomer product will occur, substantial amounts of polyethylene are formed and reactor fouling will occur after about 2 hours and continuous operations cannot be continued. The minimum amount of water from a practical viewpoint is considered to be a $Zr/H_2O$ mole ratio of 50 to 1.

The relative amounts of the two catalysts used in the present invention are somewhat variable with a mole ratio range of second component catalyst to first component catalyst of about 1 to 1 up to about 50 to 1, the preferred range being about 10 to 1 up to about 25 to 1.

The feedstock used may be pure ethylene or mixtures of ethylene with inert gases. Very minor proportions of other olefins may be present but these will tend to cause the production of unwanted olefin copolymers with attendant loss of conversion and linearity.

During the course of the reaction, the mole ratio of ethylene feedstock to oligomerization product should be greater than about 0.8 to minimize copolymerization reactions and maintain the desired high degree of linearity, and the preferred ratio is greater than 2.0.

In a preferred method of operating the process of the present invention, very minor proportions of hydrogen are introduced into the system in order to minimize the production of unwanted high molecular weight polyethylene, i.e., polyethylene of molecular weight 10,000 or more. It has been found that the hydrogen will selectively alter or suppress those catalyst moieties in the system which tend to produce such high molecular weight polyethylene. The use of about 0.02 to 1 weight percent hydrogen based on the weight of ethylene feedstock is effective to reduce or substantially eliminate such high molecular weight polyethylene such that the amount of high molecular weight polyethylene is less than 0.1 weight percent of total product. The hydrogen may be introduced with the ethylene feedstock or fed into the reactor directly or in solution under pressure.

The oligomerization product is isolated using conventional procedures such as aqueous caustic catalyst quench followed by water washing and final product recovery by distillation.

The invention is further illustrated by the following Examples which are not to be considered as limitative of its scope.

EXAMPLE 1

Zirconium tetrachloride powder 80.0g, 0.343 mole, was placed in a dry glass vessel under a dry argon atmosphere. Next 125.0g of dry n-heptane solvent was added. The resulting slurry was stirred while dry isodecyl acetate (mixed isomers sold as Exxate ® 1000 by Exxon Chemical Company), 70.0g, 0.318 mole, was added dropwise over 10 minutes. There was an exotherm to about 45° C. while the $ZrCl_4$ dissolved producing a hazy, pale yellow solution. This was filtered through a dry medium porosity glass fritt under argon and the fritt rinsed with 7.2g dry heptane. The combined rinse and filtrate weighed 282.2g and consisted of a clear, pale yellow solution that contained 28.3 wt. % $ZrCl_4$, in the form of a soluble complex with the isodecyl acetate.

EXAMPLE 2

The experiment of Example was repeated using 10.0g $ZrCl_4$, 42.9m mole, and 13.9g of dry 1-decene as solvent. Isodecyl acetate mixed isomers (Exxate ® 1000), 9.46g, 42.9m mole, was added with stirring over 3 minutes producing a pale yellow hazy solution which was allowed to stand 24 hours. A clear, pale yellow solution standing over a few milligrams of settled out precipitate resulted. A sample of the solution was then withdrawn with a syringe for testing after 24 hours (see Example 5B) and again after 35 days (see Example 5C). It contained 30.0 wt. % $ZrCl_4$

EXAMPLE 3

The experiment of Example 1 was repeated using 4.33g $ZrCl_4$, 18.6 mmole, and 256.7g n-heptane solvent. Methyl n-decanoate, 3.47g, 18.6m mole, was added over 3 minutes and the mixture was stirred for one hour. Filtering and rinsing the filter with 30.0g n-heptane gave 294g of clear, pale yellow filtrate that was 1.47 wt. % $ZrCl_4$

EXAMPLE 4

The experiment of Example 1 was repeated using 2.33 g $ZrCl_4$, 10.0 mmole, and 230g n-heptane solvent. n-Hexyl acetate, 1.44g, 10.0m mole, was added over 3 minutes and the mixture stirred for one hour. Filtration gave a clear nearly colorless solution with only a trace of insolubles on the filter. The filtrate was warmed to about 40.C and vacuum stripped to remove about one-half of the solvent. On standing and slowly cooling, colorless needle crystals grew, M.P. 98 to 98.5° C., which gave the correct elemental analysis for and adduct. An x-ray structure analysis was determined on these crystals and it indicated that the compound has a dimeric structure as follows: $[ZrCl_4.CH_3COOC_6H_{13}]_2$

EXAMPLES 5A-D

A series of ethylene oligomerizations were conducted utilizing as catalyst the adducts prepared in Examples 1, 2 and 3 and diethylaluminium chloride (DEAC) as the co-catalyst. The detailed process conditions and results are shown on the following table. Toluene solvent was used in all runs. In all cases, products were prepared having a linearity greater than 90 mole %.

The ethylene oligomerizations were conducted in a 1-liter stirred autoclave at 130° C. and 1000 psig. Reactor volume was controlled at about 500 cc by a dip leg which served as the reactor exit. The autoclave was electrically heated and oil cooled. Pressure and temperature were automatically controlled. Polymer grade ethylene was compressed to about 1500 psig from a bank of 1200 psig cylinders. Before compression, the ethylene was treated with $Cu_2O$ at 300° F. to remove oxygen. After compression, the ethylene gas was passed over a bed of molecular sieves to remove water to less than 1 ppmv. The moisture content was monitored continuously using aluminum oxide sensors. Ethylene was fed continuously at a measured rate to the reactor during the test runs. Reaction solvent was dried over sieves to less than 1 ppmw and then metered continuously into the reactor. Catalyst and co-catalyst solutions were prepared in a dry box using heated and evacuated glassware to insure minimum water contamination. The zirconium catalyst was diluted in dry solvent (solvent dried to less than 1 ppmw over molecular sieves) to a concentration of about $20 \times 10^{-6}$ gram moles of zirconium per gram of solution. The solutions were then transferred to the reactor feed tanks and held under a nitrogen blanket. The Zr catalyst solution was fed to the reactor at 10 to 100 cc/hr. The aluminum co-catalyst solutions were prepared from 20% by weight stock solutions obtained from a supplier. Again, dilution solvent was dried to less than ppm water content before using. Co-catalyst was generally diluted to about $200 \times 10^{-6}$ gram moles of aluminum per gram of solution. The diluted solution was transferred to the reactor at 10 to 100 cc/hr. A test run was started by feeding solvent, ethylene, and cocatalyst to the reactor during a heat-up period lasting up to several hours. Then, the Zr catalyst feed was started. A run balance period for data collection was started after steady state was achieved, generally 1-2 hours after the oligomerization was initiated, as noted by the reaction temperature.

TABLE

EXAMPLES 5A-D

| Example | Solvent g/hr. | Ethylene, g/hr. | Zr Moles/hr. $\times 10^6$ | DEAC Moles/hr. $\times 10^6$ | Mole Ratio Al/Zr | T° C. | psig | Residence Time, Mins. | kg Product Per g. Zr | $\overline{Mn}$ Product |
|---|---|---|---|---|---|---|---|---|---|---|
| 5A Adduct of Example 1 | 835 | 830 | 171 | 2429 | 14.2 | 131 | 999 | 14.5 | 24.8 | 108.6 |
| 5B Adduct of Example 2 | 1010 | 830 | 273 | 2575 | 9.4 | 150 | 999 | 15.2 | 12.8 | 130.0 |

TABLE-continued

EXAMPLES 5A-D

| Example | Solvent g/hr. | Ethylene, g/hr. | Zr Moles/hr. $\times 10^6$ | DEAC Moles/hr. $\times 10^6$ | Mole Ratio Al/Zr | T° C. | psig | Residence Time, Mins. | kg Product Per g. Zr | $\overline{M_n}$ Product |
| --- | --- | --- | --- | --- | --- | --- | --- | --- | --- | --- |
| 5C Adduct of Example 2 | 960 | 830 | 279 | 2109 | 7.6 | 150 | 1003 | 15.2 | 13.1 | 138.2 |
| 5D Adduct of Example 3 | 920 | 830 | 191 | 2388 | 12.5 | 130 | 1000 | 15.5 | 15.9 | 94.4 |

EXAMPLE 6

$ZrBr_4$ (4.11 g, 10 mmole) was slurried in 14 g dry n-heptane under argon and 2.5 g (10 mmole) of isodecyl acetate mixed isomers (Exxate ® 1000) was added dropwise and most of the $ZrBr_4$ dissolved within a few minutes. Only 0.10 g of unreacted $ZrBr_4$ residue remained, indicating formation of a soluble adduct.

EXAMPLE 7

$ZrCl_4$ (2.33 g. 10 mmole) was slurried in 102.5 g of dry n-heptane. Addition of 1.30 g (10 mmole) of dry dibutyl ether with stirring gave a micro crystalline white precipitate. Warming the slurry to about 45° C. re-dissolved about half the solid which crystallized as needle crystals upon cooling. The adduct complex which formed had a solubility of about 1 g in 100 g heptane at 45° C.

EXAMPLE 8

To 29.33 g of $ZrCl_4$ (125.9 mmole) was added 58 g dry n-heptane. Then 25.67 g of n-decyl acetate (128.1 mmole) was added with stirring over 20 seconds. The slurry temperature increased to about 45° C. as the $ZrCl_4$ reacted giving a hazy pale yellow solution. On cooling to about 30° C., the product separated as white colored, needle shaped mirco crystals which had a solubility at 35° C. of about 5.3 per 100 g of n-heptane.

EXAMPLE 9

(a) 2.33 g of $ZrCl_4$ (10 mmole) was slurried in 15 g of dry o-xylene and 1.56 g of n-decanal (10 mmole) was added dropwise with mixing. A clear dark red solution resulted with an exotherm to about 50° C. After standing overnight red crystals separated from solution indicating adduct formation between $ZrCl_4$ and the aldehyde.

(b) Following the procedure of Example 9 (a) above, an adduct was formed using 10 mmole of n-dodecyl amine.

(c) Following the procedure of Example 9 (a) above, an adduct was formed using 10 mmole of tri-n-hexyl amine.

Each of the foregoing Examples provided hydrocarbon soluble $ZrCl_4$ adducts suitable as catalysts for oligomerization of ethylene.

EXAMPLE 10

Comparative oligomerizations were conducted both with and without the addition of hydrogen to evaluate its effect upon the production of unwanted high molecular weight polyethylene. The solvents, catalysts and general conditions were the same as Examples 5A-D. The reaction temperature for these experiments was 130° C., the pressure was 1000 psig, the mole ratio of Al to Zr was 13.7 and the residence times were 22 minutes for Example 10 (a) which did not use $H_2$ and 23 minutes for Example 10 (b) in which there was present 1% $H_2$ based upon the weight of the ethylene feedstream. Otherwise all conditions were the same.

For Example 10 (a) a linear oligomer product having an Mn of 109 was produced at a 69% conversion of ethylene. The yield of polymeric material was 0.030 g per 100 g of product, and of this, about 20% by weight was polyethylene of molecular weight 10,000 or greater.

For Example 10 (b), which utilized hydrogen addition, a linear oligomer product was produced having an Mn of 115 at a conversion of 66% ethylene. The yield of polymeric material was 0.028 g per 100 g of product but no polyethylene was detected having a molecular weight greater than 1600.

EXAMPLE 11

(a) 1.67 g (10 mmole) of n-undecane nitrile was reacted with 2.33 g (10 mmole) of $ZrCl_4$ in 15.0 g of o-xylene solvent. A pale yellow solution was formed within 3 to 5 minutes indicating the formation of a soluble complex.

(b) 2.40 g (10 mmole) of n-decanoyl chloride was reacted with 2.33 g (10 mmole) of $ZrCl_4$ in 15.0 g of o-xylene. A red solution was formed within 3 to 5 minutes indicating the formation of a soluble complex.

(c) 1.91 g (10 mmole) n-decanoyl chloride was reacted with 2.33 g (10 mmole) $ZrCl_4$ in 15.0 g o-xylene. A yellow solution was formed within 3 to 5 minutes indicating the formation of a soluble complex.

Each of these reactions was exothermic, the reaction mixture temperatures increased from 25° C. to about 50° C.

EXAMPLES 12-17

A series of oligomerizations were conducted using catalysts prepared from six different organic compounds used to form an adduct with $ZrCl_4$. The procedure is given below with respect to the organic compound of Example 12, isodecyl acetate, sold as Exxate ® 1000 by Exxon Chemical Company, which is a mixture of isodecyl acetate isomers.

EXPERIMENTAL PROCEDURE FOR EXAMPLES 12-17

A dry 100 ml. three necked flask fitted with an inlet valve for argon, a pressure equalized dropping funnel, and an ethylene gas sparger was charged with 37 g dry p-xylene and 2.0 g of a p-xylene solution containing 0.48 g of $ZrCl_4$ in the form of an equimolar complex with isodecylacetate, Exxate ® 1000. The dropping funnel was then charged with 20 g of 20% by weight solution of diethylaluminum chloride (DEAC) in heptane. The contents of the flask were heated to 70 to 80° C. and ethylene gas sparged into the solution. The gas out-flow was through the top of the dropping funnel via a stopcock attached to an argon line and mercury bubbler vent. The DEAC solution was then added over about 5 minutes to the flask forming an initially yellow solution that turned red and then red-brown. The mixture was then cooled and carefully added with stirring to 200 ml. water. The mixture was then transferred to a separatory funnel, shaken, and the colorless organic layer separated and filtered. A gas chromatographic (GC) analysis of this solution showed the presence of the listed alpha-olefins in the peak area percents given below. The other complexes liisted below were formed in the flask by adding the given amount of organic compound to 0.48 g of $ZrCl_4$ in 20 g p-xylene. After the complex was formed and the $ZrCl_4$ dissolved, the test was contined as above.

Table for Examples 12-17

| Example | Organic Compound | Amount | GC Area % Olefin A | B | C | D |
|---|---|---|---|---|---|---|
| 12 | Exxate 1000 | 0.41 g | 1.015 | 0.038 | 0.009 | trace |
| 13 | n-Decylamine | 0.38 g | 1.010 | 0.037 | 0.012 | 0.002 |
| 14 | n-Decanoic acid chloride | 0.40 g | 0.873 | 0.022 | 0.007 | trace |
| 15 | n-Decyl succinic anhydride | 0.50 g | 1.243 | 0.055 | 0.017 | 0.003 |
| 16 | Di-n-butyl ether | 0.27 g | 1.113 | 0.042 | 0.015 | 0.003 |
| 17 | n-Decyl aldehyde | 0.32 g | 0.493 | 0.021 | 0.002 | none |

Olefin A: 1-butene
B: 1-hexene
C: 1-octene
D: 1-decene

What is claimed is:

1. An catalyst composition consisting essentially of a mixture in solution of (a) an adduct of $ZrCl_4$ with an acetate ester of the formula $CH_3COOR$ where R represents alkyl of 6 to 16 carbon atoms and the mol ratio of acetate ester to zirconium is about 0.9 to 1 up to about 2 to 1 and (b) an alkyl metal selected from the group consisting of $R_2AlX$, $RAlX_2$, $R_3Al_2X_3$, $R_3Al$ and $R_2Zn$ where R is $C_1$-$C_{20}$ alkyl and X is Cl or Br.

2. The composition of claims 1 wherein the alkyl metal is diethyl aluminum chloride, ethyl aluminum dichloride and mixtures thereof.

3. The composition of claim 1 wherein the solution comprises a solvent selected from the group consisting of $C_2$-$C_{100}$ alpha-olefins and aromatic, aliphatic and halogenated aromatic solvents.

4. The composition of claims 1, 2 or 3 wherein the mole ratio of said alkyl metal to said adduct is from about 1 to 1 u to about 50 to 1.

* * * * *